United States Patent [19]

Gamba et al.

[11] 4,415,564

[45] Nov. 15, 1983

[54] PHARMACEUTICAL PREPARATION FOR TREATING GLAUCOMA AND OCULAR HYPERTENSION

[75] Inventors: Giancesare Gamba, Nyon, Switzerland; Luciano Bonomi, Verona, Italy

[73] Assignee: Dispersa AG, Winterthur, Switzerland

[21] Appl. No.: 390,110

[22] Filed: Jun. 21, 1982

[30] Foreign Application Priority Data

Jun. 30, 1981 [GB] United Kingdom ............... 8120141

[51] Int. Cl.³ .............................................. A61K 31/33
[52] U.S. Cl. ................................................ 424/244
[58] Field of Search .......................................... 424/244

[56] References Cited

U.S. PATENT DOCUMENTS 4,164,570  8/1979  Clough et al. .................... 424/175

OTHER PUBLICATIONS

Chem. Abst. 79, 11173(w) (1973)–Bozhefatow et al.
Chem. Abst. 82, 51541(c) (1975)–Lamble.
Chem. Abst. 87, 127,126(x) (1977)–Wettrell et al.
Chem. Abst. 90, 197,831(j) (1979)–Jablenski et al.

*Primary Examiner*—Douglas W. Robinson
*Attorney, Agent, or Firm*—Michael W. Glynn

[57] ABSTRACT

Pharmaceutical preparations for treating glaucoma and ocular hypertension, containing guanethidine or a pharmaceutically acceptable salt thereof and a specific $\beta_2$-receptor agonist in relative quantities of 20:1 to 1:5 in an aqueous solution.

8 Claims, No Drawings

PHARMACEUTICAL PREPARATION FOR TREATING GLAUCOMA AND OCULAR HYPERTENSION

The present invention relates to a pharmaceutical preparation for treating glaucoma and the increase of the intraocular pressure over the normal value as a state of disease.

A number of substances or combinations of substances have already been used or suggested for the treatment of this disease which can severely impair the vision of the human eye.

Among these substances is the sympatholytic drug guanethidine (USAN, BAN, DCF) and its combination with epinephrine, i.e. a broad sprectrum sympathomimetic agent stimulating $\alpha$-, $\beta_1$- and $\beta_2$-receptors simultaneously. Other known substances for treating this disease are a number of sympathomimetic drugs. However, broad spectrum sympathomimetic drugs for this use show a number of undesirable side effects, like mydriasis and conjunctival hyperemia.

The pharmaceutical preparation for treating glaucoma and ocular hypertension according to the present invention contains guanethidine or a pharmaceutically acceptable salt thereof and a specific $\beta_2$-receptor agonist in relative quantities of 20:1 to 1:5 in an aqueous solution.

Among the $\beta_2$-receptor agonists suitable for the purpose of the present invention are carbuterol, isoetharine, metaproterenol (orciprenaline BAN, DCF), quinterenol (quinprenaline DCI rec.). albuterol (salbutamol BAN, DCF), sulfonterol, pirbuterol and particularly terbutaline. All names are United States adopted names (USAN), but differing names are added in brackets, where they exist. These active substances can be present as racemates or as pharmacologically active optical antipodes; both forms can of course be used for the purpose of the present invention. Moreover, these active substances can also be used as prodrugs (for example: ibuterol sulphate).

Guanethidine and the specific $\beta_2$-receptor agonists can be used as free bases or, preferably, in the form of pharmaceutically acceptable salts, such as e.g., the hydrochlorides, tartrates, bitartrates and, in particular, the sulfates. Because of the close relationship between the novel compounds in the free form and in the form of their salts, whatever is stated in this specification in respect of the free compounds and in respect of the salts also applies by analogy to the corresponding salts as to the free compounds respectively.

The relative quantities of the two active substances in the combination according to the invention is preferably from 10:1 to 1:2, especially from 7:1 to 1:1.5 and in particular from 5:1 to 1:1 and specifically about 1:1.

The combination of active substances according to the present invention offers unforeseeable advantages in treating glaucoma and ocular hypertension.

The use of guanethidine alone for this purpose is questionable, because at effective doses there are disturbing side-effects, like conjunctival redness, headache, ptosis of the upper lid.

The use of a $\beta_2$-receptor agonist alone for the purpose of this invention is known, but a useful effect can only be achieved with a solution of at least 0.15% of active substance (terbutaline on rabbits).

It would have been expected that the two active substances would act antagonistically, i.e. the sympatholytic drug (guanethidine) would counteract the action of the sympathomimetic drug (e.g. terbutaline).

However, the experiment showed surprisingly that this is not the case. Rather, the opposite occurs; as with the new combination of the present invention a useful therapeutic effect is achieved at concentrations of each of the active ingredient at which the latter are inactive if used alone. This can be seen from the following table, which gives the pressure reduction (mm Hg) within 1 hour and 10 minutes after the installation of each drug or of combinations in one eye, the other eye serving as control.

| Substance(s) (as sulfates) | concentration | effect (mm Hg) |
|---|---|---|
| guanethidine | 1.0% | −2.17 (p < 0,05) |
|  | 0.3% | −1.00 (p < 0,05) |
|  | 0.1% | +0.17 (p < 1,00) NS |
| terbutaline | 0.15% | −4.50 (p < 0,001) |
|  | 0.05% | −1.50 (p < 0,05) |
|  | 0.015% | −.83 (p < 1,00) NS |
| guanethidine | 0.3% | −4.17 (p < 0,001) |
| terbutaline | 0.015% | |
| guanethidine | 0.3% | −6.00 (p < 0,001) |
| terbutaline | 0.05% | |
| guanethidine | 0.1% | −8.83 (p < 0,001) |
| terbutaline | 0.15% | |
| guanethidine | 1.0% | −11,50 (p < 0,001) |
| terbutaline | 0.15% | |

NS = not significant

These results have been obtained from tests on rabbits according to the method described by L. Bonomi et al. in Investigative Ophthalmology 15, 781–784 (1976).

According to the above table, the concentrations of each of the active substances in the first and the second combination are 3 times and in one case even 10 times lower than the active dose of each of the substances used alone, and in spite of these lower concentrations the combinations cause a stronger reduction of pressure. These results prove the existence of a strong synergism. The effect obtained with the third combination shows that a completely ineffective concentration of guanethidine substantially enhances the effect of an effective concentration of terbutaline. The effect is still more increased if, as in the fourth combination, effective concentrations of each component are used. It is further noteworthy that the synergism can be observed over a broad range of dose relations, as the relation is 20:1 in the first, and 1:1,5 in the third combination.

Due to the low concentrations of active substances in the combinations according to the present invention, side-effects as described above for effective doses of guanethidine alone, have not occurred.

The carriers and adjuvants for the pharmaceutical preparations according to the present invention are the usual ones for this type of medicament, namely those used for the preparation of aqueous solutions to be instilled in the eye. Such solutions can contain antioxidants, e.g. sodium pyrosulfite, preservative agents, e.g. sodium mercurothiolate, benzalconium chloride or 2-phenylethyl alcohol, buffers and/or physiological salts, such as sodium salts of phosphoric acid, citric acid or sodium chloride, respectively (in an amount sufficient to obtain a cryoscopic point similar to that of the tears) and sterile water.

The concentrations of the active ingredients in the pharmaceutical preparations according to the present invention are in the order of 0.1 to 1% of guanethidine or of a pharmaceutically acceptable salt thereof and 0.015–0.5%, especially 0.05–0.5% of the $\beta_2$-receptor agonist, e.g. terbutaline, or of a pharmaceutically acceptable salt thereof, preferably about 0.1 to about 0.5% of each and most advantageously about 0.3% of each. The preparation is applied by one or two drops per eye at regular intervals of 1–3 (preferable 2) times per day. The invention also pertains to a method of treating glaucoma and ocular hypertension which comprises administering to a person requiring such treatment a pharmaceutical preparation as defied above.

The invention is illustrated by the following Examples:

EXAMPLE 1

For obtaining 10,000 bottles of 10 ml of eye drop solution containing 0.3% of each active components, 0.31 kg of disodium phosphate, 0.15 kg of citric acid, 0.35 kg of sodium chloride, 0.10 kg of sodium pyrosulfite, 0.01 kg of benzalconium chloride, 0.30 kg of guanethidine sulfate and 0.30 kg of terbutaline sulfate are dissolved under stirring and nitrogen atmosphere in 98.8 kg distilled water.

Thereafter, the solution is filtered under sterile conditions through a membrane filter (pore diameter: 0.2 μm) and then filled into 10 ml bottles under septic conditions.

EXAMPLE 2

For obtaining 10,000 bottles of 10 ml of eye drop solution, 0.003 kg of sodium mercurothiolate [cp. DCF, sodium 2-(ethylmercurithio)-salicylate], 0.610 kg of sodium chloride, 0.30 kg of guanethidine sulfate and 0.30 kg of terbutaline sulfate are dissolved under stirring and under nitrogen atmosphere in 99.1 kg distilled water.

The solution is sterilized in an autoclave at 120° C. during 20 minutes, subsequently filtered through a filter membrane (pore diameter: 0.2 μm) and filled in 10 ml bottles under aseptic conditions.

EXAMPLE 3

2.0 kg of polyvinyl alcohol is dissolved in 97.0 kg of boiling distilled water. After cooling to room temperature 0.40 kg of 2-phenylethyl alcohol, 0.385 kg of disodium phosphate, 0.265 kg of citric acid, 0.30 kg of sodium chloride, 0.10 kg of sodium pyrosulfite, 0.30 kg of terbutaline sulfate and 0.30 kg of guanethidine sulfate are added to this eye drop solution.

Thereafter the solution is filtered under sterile conditions through a membrane filter (pore diameter: 0.42 μm) and then filled into 10 ml bottles under aseptic conditions.

In this way 10,000 bottles of a viscous solution are obtained.

I claim:

1. Pharmaceutical composition for treating glaucoma and ocular hypertension, comprising guanethidine or a pharmaceutically acceptable salt thereof and terbutaline or a pharmaceutically acceptable salt thereof in relative quantities of 20:1 to 1:1.5 in an aqueous solution.

2. Pharmaceutical composition according to claim 1, characterised by relative quantities from 10:1 to 1:2.

3. Pharmaceutical composition according to claim 1, characterised by relative quantities from 5:1 to 1:1.

4. Pharmaceutical composition according to claim 1, characterised by relative quantities of about 1:1.

5. A pharmaceutical composition according to claim 1 in the form of an aqueous solution comprising pharmaceutically acceptable salts of guanethidine and of terbutaline as active ingredients in concentrations of 0.1–1% of the first and 0.015–0.5% of the latter ingredient.

6. A pharmaceutical composition in the form of an aqueous solution according to claim 5, containing each active ingredient in a concentration of 0.1 to 0.5%.

7. A pharmaceutical composition in the form of an aqueous solution according to claim 5, containing each active ingredient in a concentration of 0.3%.

8. A method of treating glaucoma or ocular hypertension which comprises topically applying to the eye of a person requiring such treatment a pharmaceutical composition according to claim 1.

* * * * *